United States Patent
Funahashi et al.

(10) Patent No.: US 7,122,256 B2
(45) Date of Patent: Oct. 17, 2006

(54) STYRYL COMPOUND AND ORGANIC ELECTROLUMINESCENCE DEVICE

(75) Inventors: Masakazu Funahashi, Chiba (JP); Hiromasa Arai, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 121 days.

(21) Appl. No.: 09/943,578

(22) Filed: Aug. 31, 2001

(65) Prior Publication Data
US 2003/0044640 A1    Mar. 6, 2003

(30) Foreign Application Priority Data
Sep. 1, 2000    (JP) .............................. 2000-265544

(51) Int. Cl.
*H05B 33/12*    (2006.01)
(52) U.S. Cl. .................. 428/690; 428/917; 257/40; 257/E51.051; 313/504; 313/506; 564/426; 564/433; 564/434
(58) Field of Classification Search ................ 428/690, 428/917; 564/429, 433, 434, 426; 313/504, 313/503, 506
See application file for complete search history.

(56) References Cited

U.S. PATENT DOCUMENTS 4,666,810 A    5/1987    Umehara et al. ............. 430/71

(Continued)

FOREIGN PATENT DOCUMENTS

EP    0 317 233 A2    5/1989

(Continued)

Primary Examiner—Rena Dye
Assistant Examiner—Carnie Thompson
(74) Attorney, Agent, or Firm—Steptoe & Johnson LLP

(57) ABSTRACT

Novel styryl compounds represented by the following general formulae (1) and (2):

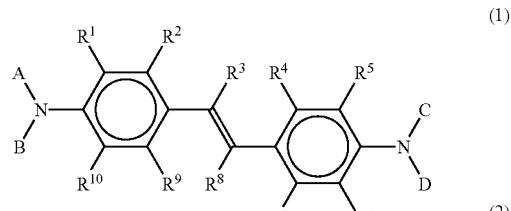

(1)

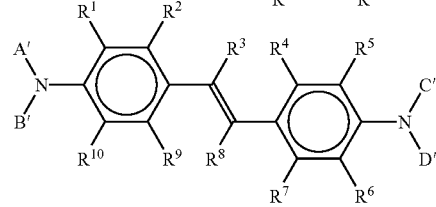

(2)

wherein $R^1$ to $R^{10}$ each independently represent hydrogen atom, an alkyl group, an alkoxyl group, an aryl group, an aryloxyl group, a condensed polycyclic group, a heterocyclic group, amino group, an alkylamino group, an arylamino group, cyano group, nitro group, hydroxyl group or a halogen atom, adjacent groups among groups represented by $R^1$ to $R^{10}$ may be bonded to each other and form a saturated or unsaturated carbon ring, and A, B, C, D, A', B', C' and D' each independently represent a substituted or unsubstituted alkyl group or aryl group having a specific structure; and an organic electroluminescence device comprising a film of organic compounds comprising at least a light emitting layer, wherein at least one of the layers of the film of organic compounds comprises the novel styryl compound. The organic electroluminescence device has excellent heat resistance, a high efficiently of light emission and a long life and emits blue light of a high purity. The novel styryl compounds provide the advantageous properties to the organic electroluminescence device.

8 Claims, 5 Drawing Sheets

U.S. PATENT DOCUMENTS

| | | |
|---|---|---|
| 5,667,925 A | 9/1997 | Tsuruoka et al. .............. 430/59 |
| 6,468,675 B1 * | 10/2002 | Ishikawa et al. ............ 428/690 |
| 6,489,045 B1 * | 12/2002 | Araki et al. ................. 428/690 |
| 6,534,199 B1 * | 3/2003 | Hosokawa et al. .......... 428/690 |

FOREIGN PATENT DOCUMENTS

| | | | |
|---|---|---|---|
| EP | 0 866 110 A1 | | 9/1998 |
| EP | 0 879 868 A2 | | 11/1998 |
| JP | 63-063047 A | | 3/1988 |
| JP | 3-24554 | | 2/1991 |
| JP | 4-253065 | | 9/1992 |
| JP | 4-264189 | | 9/1992 |
| JP | 06-027701 A | | 2/1994 |
| JP | 07-175238 | * | 7/1995 |
| JP | 7-249490 | | 9/1995 |
| JP | 10-125468 | | 5/1998 |
| JP | 11-008068 | * | 1/1999 |
| JP | 11-008068 A | | 1/1999 |
| JP | 11-040359 A | | 2/1999 |
| JP | 11-065140 | * | 3/1999 |
| JP | 2000-12229 | | 1/2000 |

* cited by examiner

STYRYL COMPOUND AND ORGANIC ELECTROLUMINESCENCE DEVICE

TECHNICAL FIELD

The present invention relates to a novel styryl compound and an organic electroluminescence device and, more particularly, to an organic electroluminescence device having excellent heat resistance, a high efficiently of light emission and a long life and emitting blue light of a high purity and a novel styryl compound providing the advantageous properties to the organic electroluminescence device.

BACKGROUND ART

Organic electroluminescence (referred to as EL, hereinafter) devices are used for a planar light emitting member such as a flat panel display of wall televisions and a back light of displays and the development of EL devices has been widely conducted. As an area of such development, the development of a material used for a light emitting device which emits blue light at a high efficiency and has a long life has been conducted.

For example, a stilbene compound and a device using the stilbene compound are disclosed in EP0610514. However, the disclosed device shows a poor purity of color and has a short life although blue light is emitted at a high efficiency and cannot be practically used.

For practical application of a device as a blue color pixel of a color display, specifically, it is necessary that the y-coordinate of the chromaticity be smaller than 0.18 and the half-life be 10,000 hours or longer.

DISCLOSURE OF THE INVENTION

The present invention has been made to overcome the above problem and has an object of providing an organic EL device having excellent heat resistance, a high efficiently of light emission and a long life and emitting blue light of a high purity and a novel styryl compounds providing the advantageous properties to the organic electroluminescence device.

As the result of extensive studies by the present inventors to develop the organic EL device having the above advantageous properties, it was found that, when a novel styryl compound having a specific structure is added to a film of organic compounds, the obtained organic EL device had improved heat resistance and life, achieved a high efficiency of light emission due to improved transportation of holes and electrons and emitted blue light of an improved purity. The present invention has been completed based on the knowledge.

The present invention provides a novel styryl compound represented by the following general formula (1):

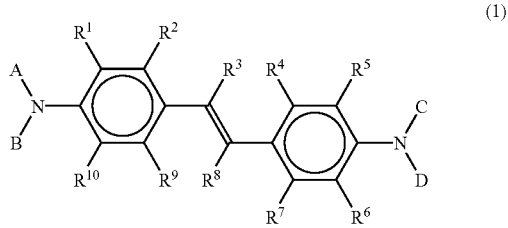

(1)

wherein $R^1$ to $R^{10}$ each independently represent hydrogen atom, a substituted or unsubstituted alkyl group having 1 to 30 carbon atoms, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^1$ to $R^{10}$ may be bonded to each other and form a saturated or unsaturated carbon ring; and A, B, C and D each independently represent a substituted or unsubstituted alkyl group having 1 to 20 carbon atoms or a substituted or unsubstituted aryl group having 6 to 40 carbon atoms, and at least two of A, B, C and D each represent a group represented by $-Ar^1-Ar^2$, $Ar^1$ representing a substituted or unsubstituted phenylene group or naphthalene group and $Ar^2$ representing a substituted or unsubstituted aryl group having 6 to 34 carbon atoms, excluding a case in which A and C represent biphenyl group and B and D represent phenyl group; and A novel styryl compound represented by the following general formula (2):

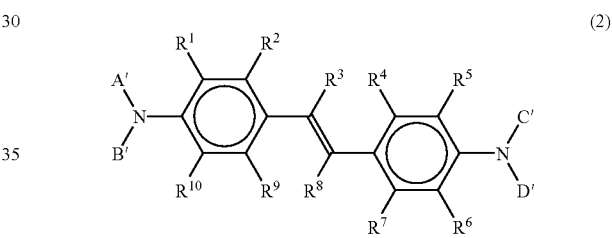

(2)

wherein $R^1$ to $R^{10}$ are as defined above; and

A', B', C' and D' each independently represent a substituted or unsubstituted alkyl group having 1 to 20 carbon atoms or a substituted or unsubstituted aryl group having 6 to 40 carbon atoms, and A' and C' each represent a substituted or unsubstituted condensed hydrocarbon group having 2 to 5 rings.

The present invention further provides an electroluminescence device comprising a pair of electrodes and a film of organic compounds which is disposed between the pair of electrodes and comprises a single layer or a plurality of layers comprising at least a light emitting layer, wherein at least one of the layers of the film of organic compounds comprises a novel styryl compound described above.

THE MOST PREFERRED EMBODIMENT TO CARRY OUT THE INVENTION

Figure 1:
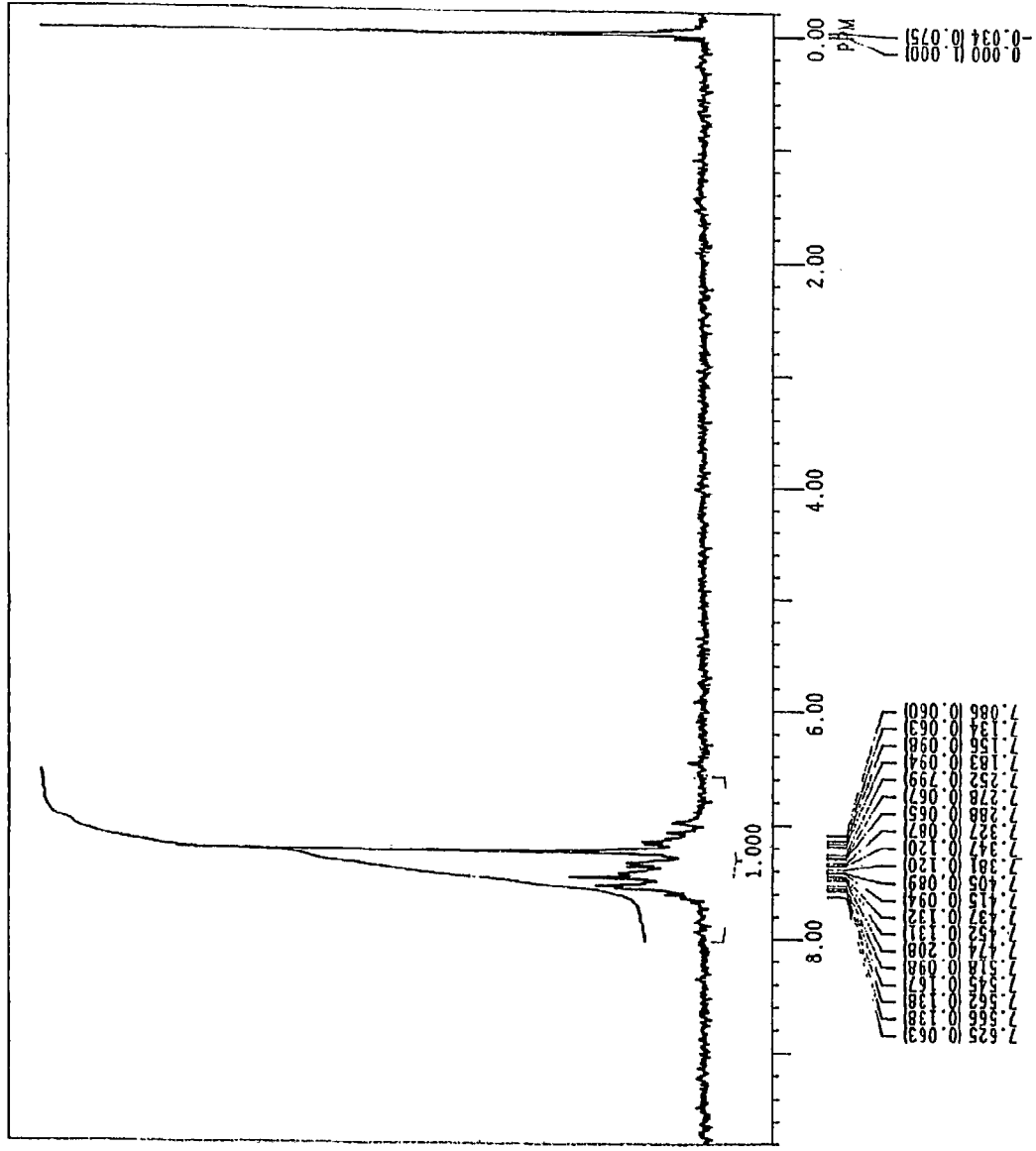
FIG. 1 shows a $^1H_{NMR}$ chart of novel styryl compound (1) of the present invention.

The novel styryl compound of the present invention is represented by the above general formula (1) or (2).

In general formulae (1) and (2), $R^1$ to $R^{10}$ each independently represent hydrogen atom, a substituted or unsubstituted alkyl group having 1 to 30 carbon atoms, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^1$ to $R^{10}$ may be bonded to each other and form a saturated or unsaturated carbon ring.

In general formula (1), A, B, C and D each independently represent a substituted or unsubstituted alkyl group having 1 to 20 carbon atoms or a substituted or unsubstituted aryl group having 6 to 40 carbon atoms, and at least two of A, B, C and D each represent a group represented by $-Ar^1-Ar^2$, wherein $Ar^1$ represents a substituted or unsubstituted phenylene group or naphthalene group and $Ar^2$ represents a substituted or unsubstituted aryl group having 6 to 34 carbon atoms. However, the case in which A and C represent biphenyl group and B and D represent phenyl group is excluded.

In general formula (2), A', B', C' and D' each independently represent a substituted or unsubstituted alkyl group having 1 to 20 carbon atoms or a substituted or unsubstituted aryl group having 6 to 40 carbon atoms, and A' and C' each represent a substituted or unsubstituted condensed hydrocarbon group having 2 to 5 rings.

The organic EL device of the present invention comprises a pair of electrodes and a film of organic compounds which is disposed between the pair of electrodes and comprises a single layer or a plurality of layers comprising at least a light emitting layer, wherein at least one of the layers of the film of organic compounds comprises a novel styryl compound described above.

It is preferable that the light emitting layer comprises the novel styryl compound described above. It is also preferable that an electron injecting layer or a hole injecting layer comprises the novel styryl compound described above.

A layer of an inorganic compound may be disposed between the light emitting layer and the electrode.

The heat resistance, the efficiency of light emission, the life and the purity of the emitted blue light of the organic EL device are improved by introducing the above novel styryl compound into at least one of the layers in the film of organic compounds because the styryl compound has an excellent fluorescent property and the fluorescent spectrum has a peak at a short wave length. Moreover, the change of the film comprising the novel styryl compound by heat is suppressed since the novel styryl compound has hydrocarbon ring groups having 8 rings or more and, occasionally, hydrocarbon ring groups having 10 rings or more and the molecular weight is high.

In the novel styryl compound of the present invention, examples of the aryl group include phenyl group, naphthyl group, anthryl group, acenaphthenyl group, fluorenyl group, phenanthryl group, indenyl group, pyrenyl group and fluoranthenyl group.

Typical examples of the novel styryl compound of the present invention are shown in the following as compounds (1) to (22). However, the novel styryl compound of the present invention is not limited to the compounds shown as the examples.

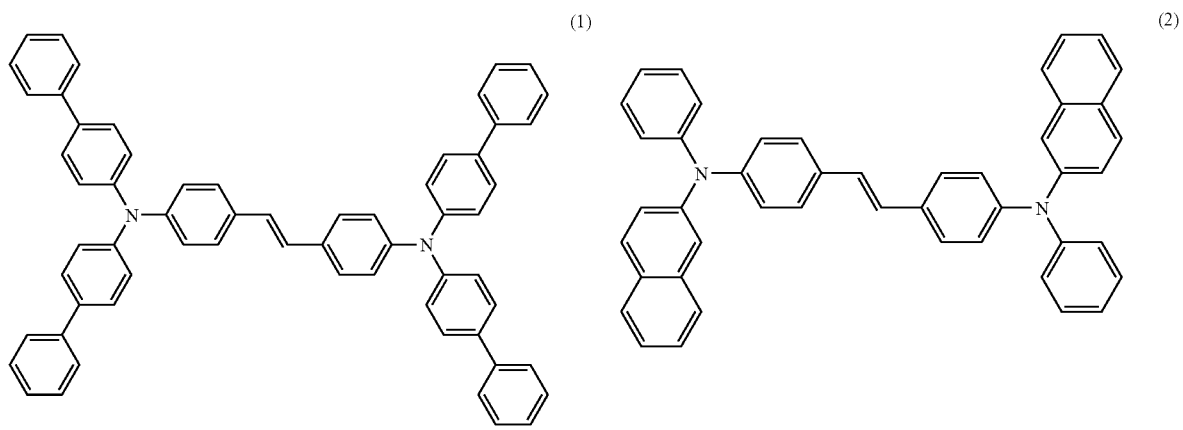

-continued
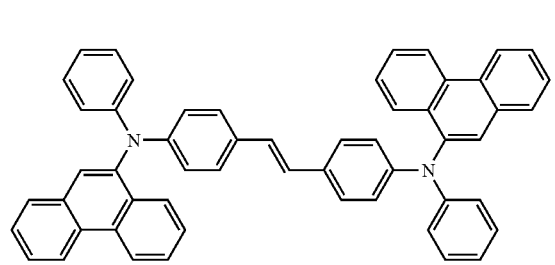
(3)
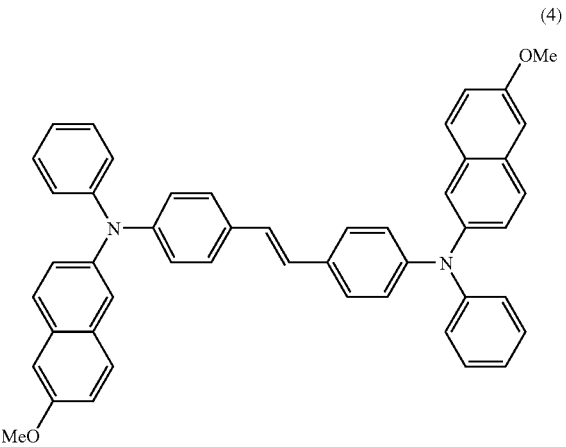
(4)
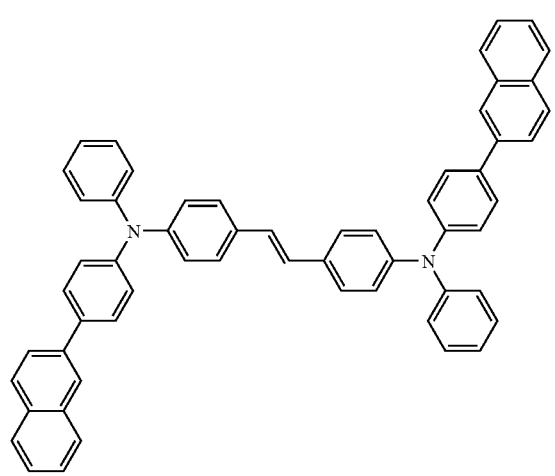
(5)
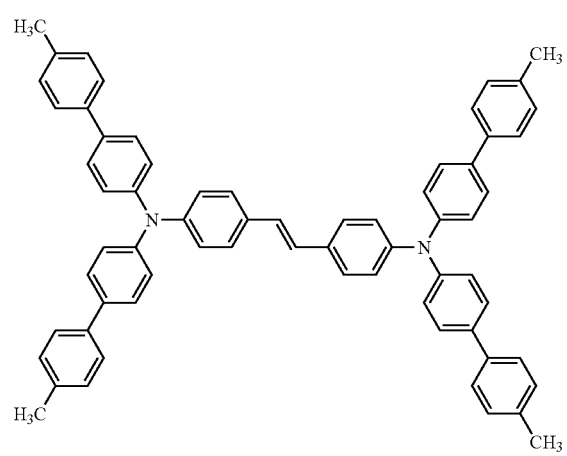
(6)
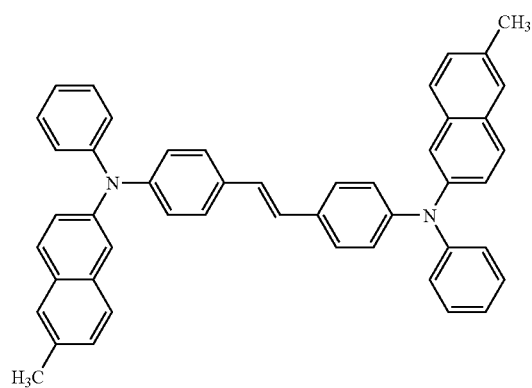
(7)

-continued
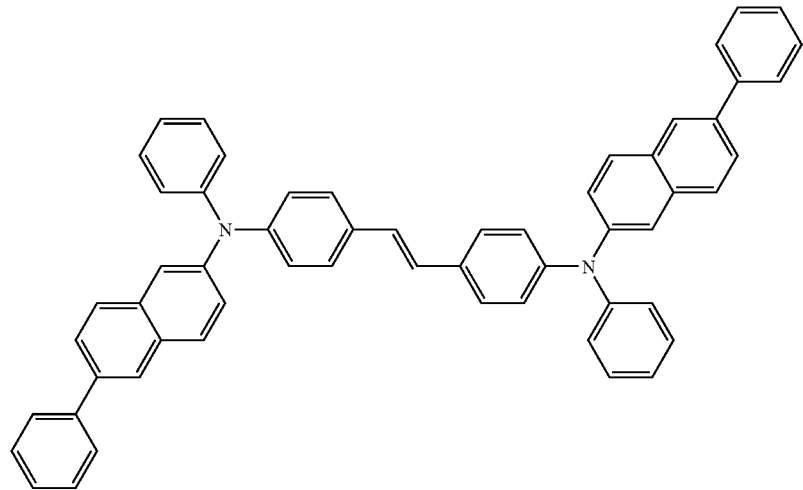
(8)
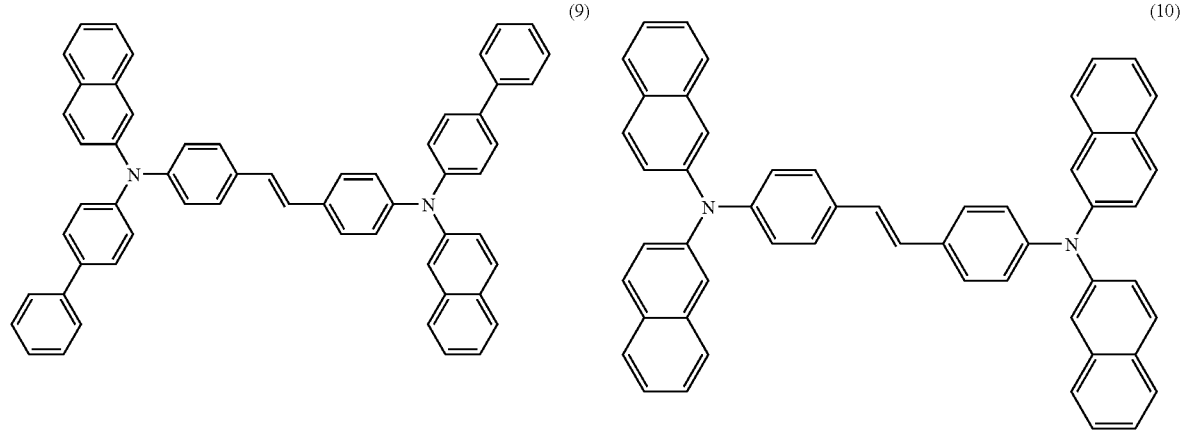
(9) (10)
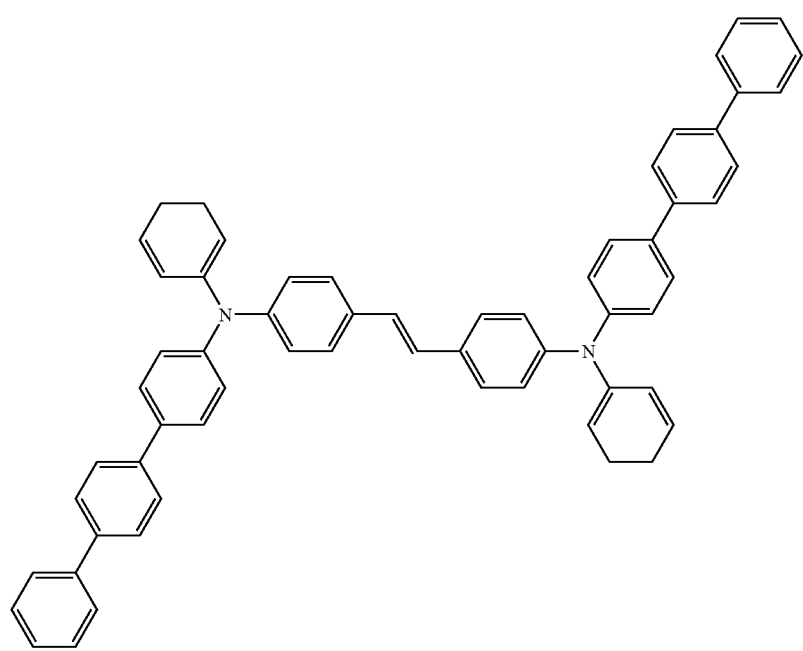
(11)

-continued
(12)
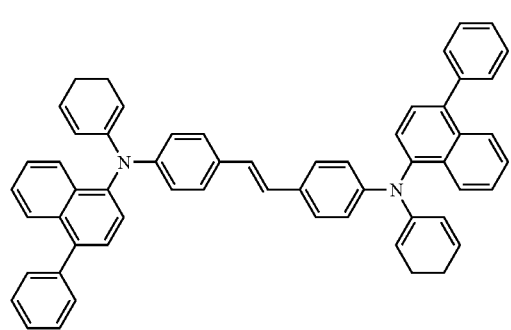
(13)
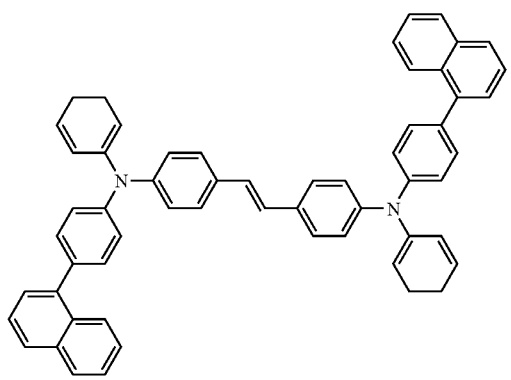
(14)
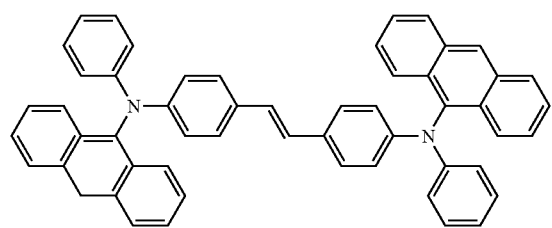
(15)
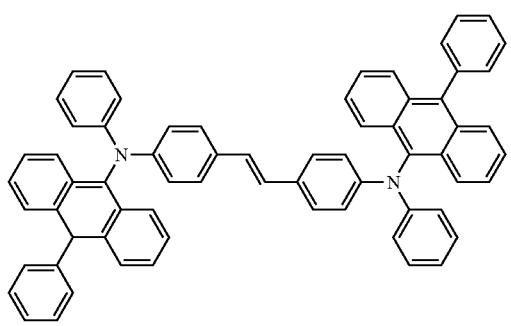
(16)
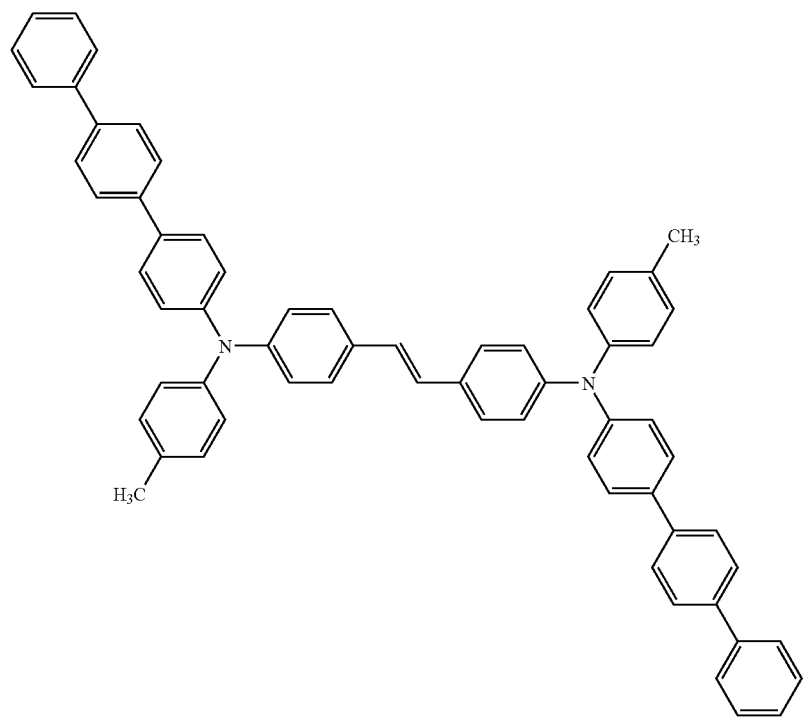

(17)
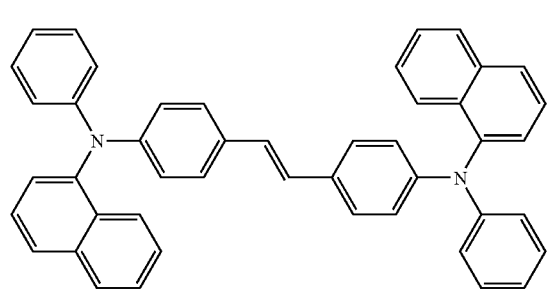
(18)
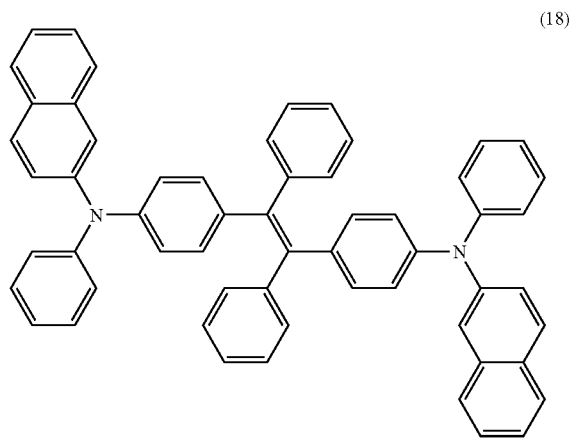
(19)
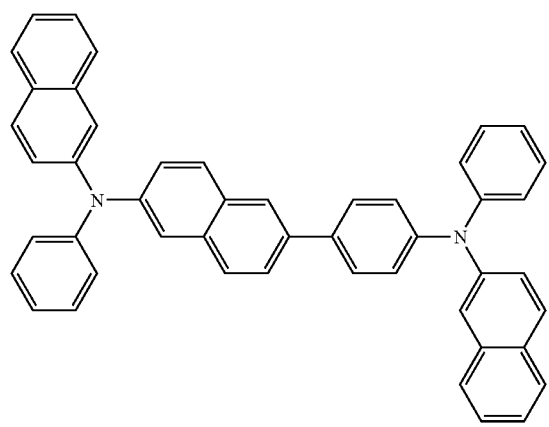
(20)
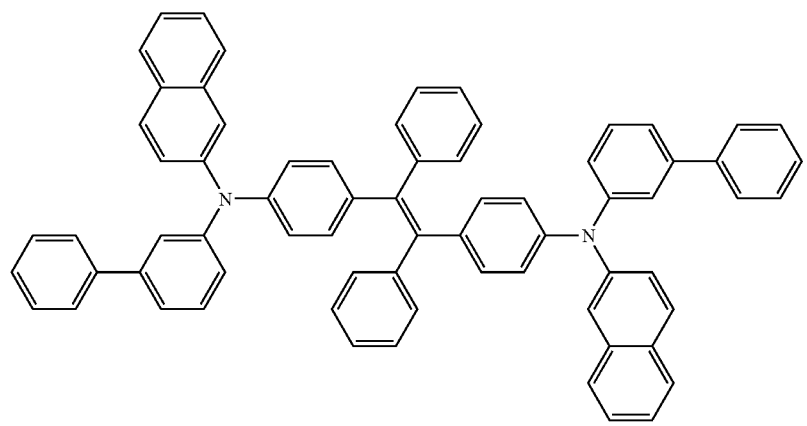

-continued

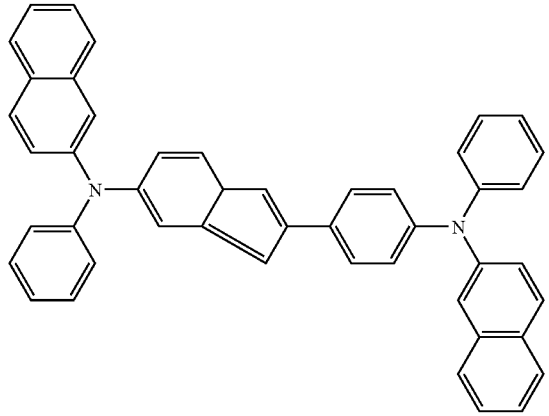
(21)

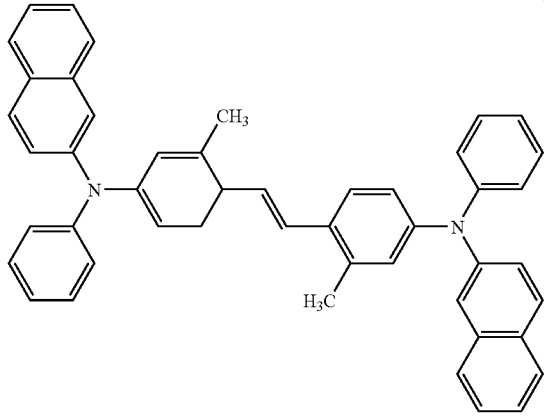
(22)

The organic EL device of the present invention is a device comprising a film of organic compounds having a single layer or a plurality of layers disposed between an anode and a cathode. When the film of organic compounds has a single layer, a light emitting layer is disposed between the anode and the cathode. The light emitting layer comprises a light emitting material and may further comprise a hole injecting material or an electron injecting material to transport holes injected from the anode or electrons injected from the cathode, respectively, to the light emitting material. However, it is preferable that the light emitting material has a very high fluorescent quantum efficiency and a combination of an excellent ability of transporting holes and an excellent ability of transporting electrons and can form a uniform thin film. When the film of organic compounds in the organic EL device has a plurality of layers, the organic EL device has a laminate structure of a plurality of layers such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

In the light emitting layer, conventional light emitting materials, doping materials, hole injection materials and electron injecting materials may further be used in addition to the novel styryl compound of the present invention. It is preferable that the novel styryl compound is used as the doping material and introduced into a layer selected from the light emitting layer, the electron injecting layer, the hole transporting layer and the hole injecting layer in a concentration of 0.1 to 20% by weight and more preferably in a concentration of 1 to 10% by weight.

By forming the organic EL device in a multi-layer structure, decreases in the luminance and the life due to quenching can be prevented. Where necessary, light emitting materials, other doping materials, hole injecting materials and electron injecting materials may be used in combination. By using other doping materials, the luminance and the efficiency of the light emission can be improved and red light or white light can be emitted. The hole injecting layer, the light emitting layer and the electron injecting layer may be each formed in a laminate structure having two or more layers. When the hole injecting layer has a laminate structure having two or more layers, a layer into which holes are injected from the electrode is called the hole injecting layer and a layer which receives the holes from the hole injecting layer and transports the holes to the light emitting layer is called the hole transporting layer. Similarly, when the electron injecting layer has a laminate structure having two or more layers, a layer into which electrons are injected from the electrode is called the electron injecting layer and a layer which receives the electrons from the hole injecting layer and transports the electrons to the light emitting layer is called the electron transporting layer. The layer is selected and used in accordance with the properties of the material such as the energy level, heat resistance and adhesion with the film of organic compounds or the metal electrodes.

As the light emitting material or a host material which can be used for the film of organic compounds in combination with the novel styryl compound, condensed polycyclic aromatic compounds can be used. Examples of the polycyclic aromatic compound include anthracene, naphthalene, phenanthrene, pyrene, tetracene, pentacene, coronene, chrysene, fluorescein, perylene, rubrene, phthaloperylene, naphthaloperylene, perynone, phthaloperynone, naphthaloperynone, diphenylbutadiene, tetraphenylbutadiene, coumarine, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, merocyanine, oxinoid compounds chelated with imidazole, quinacridone, stilbene and derivatives of the above compounds. However, the polycyclic aromatic compound is not limited to the above compounds described as the examples.

As the hole injecting material, compounds having the ability of transporting holes, exhibiting the effect of injecting holes from the anode and the excellent effect of injecting holes to the light emitting layer or the light emitting material, preventing transfer of excited particles formed in the light emitting layer into the electron injecting layer or the electron injecting material and having the excellent ability of forming a thin film are preferable. Examples of the hole injecting material include phthalocyanine derivatives, napthalocyanine derivatives, porphyrin derivatives, oxazole, oxadiazole, triazole, imidazole, imidazolone, imdazolethione, pyrazoline, pyrazolone, tetrahydroimidazole, hydrazone, acylhydrazone, polyarylalkanes, stilbene, butadiene, triphenylamines of the benzidine type, triphenylamines of the styrylamine type, triphenylamines of the diamine type, derivatives of the above compounds and macromolecular materials such as polyvinylcarbazole, polysilane and electrically conductive macromolecular compounds. However, the hole injecting material is not limited to the compounds described above as the examples.

Among the hole injecting materials which can be used in the organic EL device of the present invention, aromatic tertiary amine derivatives and phthalocyanine derivatives are more effective.

Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)phenanthrene-9,10-diamine, N,N-bis(4-di-4-tolylaminophenyl)-4-phenylcyclohexane and oligomers and polymers having the skeleton structure of the aromatic tertiary amine described above. However, the aromatic tertiary amine derivative is not limited to the compounds described above as the examples.

Examples of the phthalocyanine (Pc) derivative include phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O—GaPc. However, the phthalocyanine derivative is not limited to the compounds described above as the examples.

As the electron injecting material, compounds having the ability of transporting electrons, exhibiting the effect of injecting electrons from the cathode and the excellent effect of injecting electrons into the light emitting layer or the light emitting material, preventing transfer of excited particles formed in the light emitting layer into the hole injecting layer and having the excellent ability of forming a thin film are preferable. Examples of the electron injecting material include fluorenone, anthraquinodimethane, diphenoquinone, thiopyrane dioxide, oxazole, oxadiazole, triazole, imidazole, perylenetetracarboxylic acid, fluorenylidenemethane, anthrone and derivatives of these compounds. However, the electron injecting material is not limited to the compounds described above as the examples. The charge injecting property can be improved by adding an electron accepting substance to the hole injecting material or an electron donating substance to the electron injecting material.

In the organic EL device of the present invention, metal complex compounds and five-membered ring derivatives containing nitrogen are more effective as the electron injecting material.

Examples of the metal complex compound include (8-quinolinol)lithium, bis(8-quinolinol)zinc, bis(8-quinolinol)copper, bis(8-quinolinol)manganese, tris(8-quinolinol)aluminum, tris(2-methyl-8-quinolinol)aluminum, tris(8-quinolinol)gallium, bis(10-hydroxybenzo[h]-quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium. However, the metal complex compound is not limited to the compounds described above as the examples.

As the five-membered ring derivative containing nitrogen, derivatives of oxazole, thiazole, oxadiazole, thiadiazole and triazole are preferable. Examples of such compounds include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene. However, the five-membered ring derivative containing nitrogen is not limited to the compounds described above as the examples.

In the present invention, a layer of an inorganic compound may be disposed between the light emitting layer and the electrode to improve the charge injecting property. As the inorganic compound used for the layer of an inorganic compound, alkali metal compounds such as fluorides and oxides of alkali metals and alkaline earth compounds can be used. Examples of the inorganic compound include LiF, $Li_2O$, BaO, SrO, $BaF_2$ and $SrF_2$.

As the electrically conductive material used for the anode of the organic EL device, materials having a work function greater than 4 eV are suitable. Examples of such materials include carbon, aluminum, vanadium, iron, cobalt, nickel, tungsten, silver, gold, platinum, palladium, alloys of these metals, metal oxides used for ITO substrates and NESA substrates such as tin oxide and indium oxide and organic electrically conductive resins such as polythiophene and polypyrrole. As the electrically conductive material used for the cathode, materials having a work function smaller than 4 eV are suitable. Examples of such materials include magnesium, calcium, tin, lead, titanium, yttrium, lithium, ruthenium, manganese, aluminum and alloys of these materials. However, the materials for the electrodes are not limited to the materials described above as the examples. Examples of the alloy include magnesium/silver alloys, magnesium/indium alloys and lithium/aluminum alloys. However, the alloy is not limited to the alloys described above as the examples. The composition of the alloy is controlled by the temperature of the sources of vapor deposition, the atmosphere and the degree of vacuum and is selected suitably. The anode and the cathode may have a laminate structure having two or more layers, where necessary.

To obtain efficient light emission from the organic EL device, it is preferable that at least one face of the device is sufficiently transparent in the region of the wavelength of the light emitted by the device. It is preferable that the substrate is also transparent. The transparent electrode is prepared by using the above electrically conductive material in accordance with a suitable process such as the vapor deposition and the sputtering in a manner such that the specific transparency can be obtained. It is preferable that the electrode at the side of the light emitting face has a transmittance of the emitted light of 10% or greater. The substrate is not particularly limited as long as the substrate has a mechanical strength, shows strength at high temperatures and is transparent. Examples of the substrate include glass substrates and transparent films of resins. Examples of the transparent films include films of resins such as polyethylene, copolymers of ethylene and vinyl acetate, copolymers of ethylene and vinyl alcohol, polystyrene, polymethyl methacrylate, polyvinyl chloride, polyvinyl alcohol, polyvinyl butyral, nylon, polyether ether ketones, polysulfones, polyether sulfones, copolymers of tetrafluoroethylene and perfluoroalkyl vinyl ethers, polyvinyl fluoride, copolymers of tetrafluoroethylene and ethylene, copolymers of tetrafluoroethylene and hexafluoropropylene, poly-chlorotrifluoroethylene, polyvinylidene fluoride, polyesters, polycarbonates, polyurethanes, polyether imides, polyimides and polypropylene.

To improve the stability of the organic EL of the present invention to heat, moisture and the atmosphere, a protective layer may be formed on the surface of the device or the entire device may be coated with a silicone oil or a resin for protection.

For forming the layers in the organic EL device, any process can be selected from dry processes for film formation such as the vacuum vapor deposition process, the sputtering process, the plasma process and the ion plating process and wet processes for film formation such as the spin coating process, the dipping process and the flow coating process. The thickness of the film is not particularly limited. It is necessary that the thickness of the film be set within a suitable range. When the thickness of the film is greater than the suitable range, it is necessary that a great voltage be applied to obtain a specific output of the light and the efficiency decreases. When the thickness of the film is smaller than the suitable range, pin holes are formed and a sufficient luminance cannot be obtained when an electric field is applied. In general, it is preferable that the thickness of the film is in the range of 5 nm to 10 μm and more preferably in the range of 10 nm to 0.2 μm.

When a wet process for the film formation is used, the material for forming each layer is used for forming the thin film after the material is dissolved or dispersed in a suitable solvent such as ethanol, chloroform, tetrahydrofuran and dioxane. As the solvent, any of the above solvents can be used. In any of the layers of the organic thin films, suitable resins or additives may be used for improving the properties of the films and preventing formation of pin holes. Examples of the resin which can be used include insulating resins such as polystyrene, polycarbonates, polyarylates, polyesters, polyamides, polyurethanes, polysulfones, polymethyl methacrylate, polymethyl acrylate, cellulose and copolymers of these resins; photoconductive resins such as poly-N-vinylcarbazole and polysilane; and electrically conductive resins such as polythiophene and polypyrrole. Examples of the additive include antioxidants, ultraviolet light absorbents and plasticizers.

The organic EL device of the present invention can be used, for example, for a planar light emitting member for a flat panel display of wall televisions, a back light of copiers, printers and liquid crystal displays, a light source for instruments, a display panel and a marking light.

EXAMPLES

The present invention will be described more specifically with reference to Synthesis Examples and Examples in the following. However, the present invention is not limited to Synthesis Examples and Examples.

Synthesis Example 1

Compound (1) was synthesized in accordance with the following route of reactions:

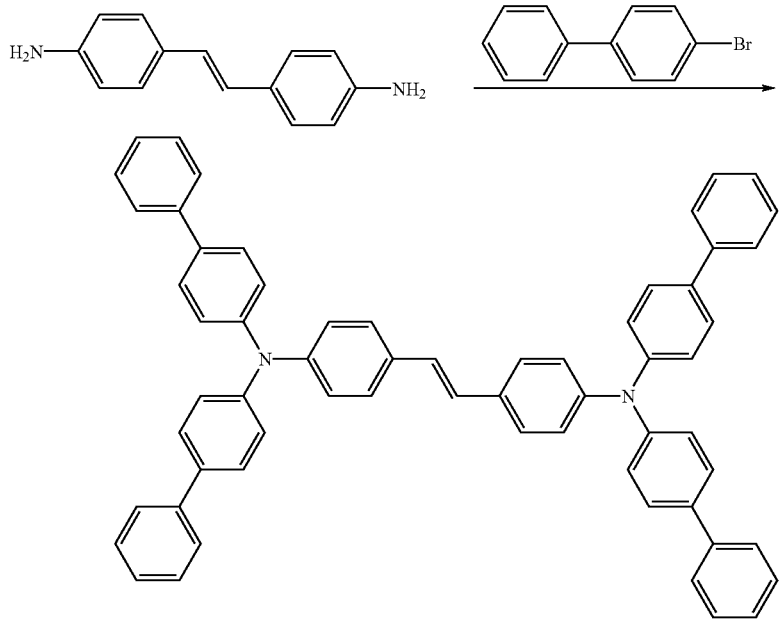

Compound (1)

Into a 200 ml three-necked flask equipped with a condenser, 2.8 g (10 mmole) of 4,4'-diaminostilbene dihydrochloride, 10.3 g (44 mmole) of 4-bromobiphenyl, 0.14 g (1.5% by mole) of tris(dibenzylideneacetone)dipalladium, 0.06 g (3% by mole) of tri-t-butylphosphine, 4.2 g (44 mmole) of sodium t-butoxide and 100 ml of dry toluene were placed under argon and the resultant mixture was stirred under heating at 100° C. for one night. After the reaction was completed, precipitated crystals were separated by filtration and washed with 100 ml of methanol and 4.9 g of a yellow powder was obtained. The obtained product was identified to be compound (1) by the measurements in accordance with NMR, IR and FD-MS (the field desorption mass spectroscopy) (the yield: 60%). The NMR chart of compound (1) is shown in FIG. 1.

Synthesis Example 2

Compound (2) was synthesized in accordance with the following route of reactions:

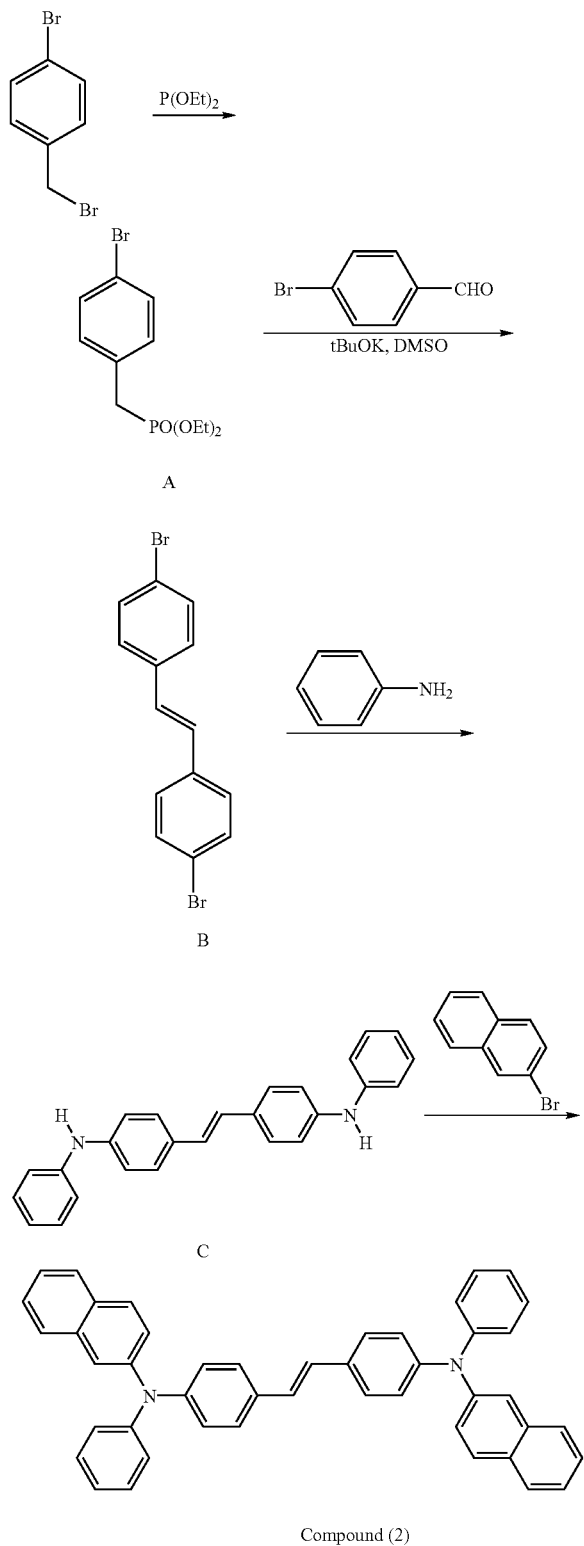

Compound (2)

Synthesis of Intermediate A

Into a flask containing a solvent, 150 g (0.6 mole) of 4-bromobenzyl bromide and 299 g (1.8 mole) of ethyl phosphite were placed and the resultant mixture was stirred under the condition of refluxing for 18 hours. After the reaction was completed, the solvent was removed from the reaction mixture by distillation under a reduced pressure. From the residue of the distillation, ethyl phosphite was removed by distillation under a further reduced pressure (bp. 75° C./2 torr) and 185 g (the yield: 100%) of the object substance was obtained as the residue of the distillation.

Synthesis of Intermediate B

Into a solution containing 185 g (0.6 mole) of intermediate A, 134 g (0.72 mole) of 4-bromobenzaldehyde and 1850 ml of dimethylsulfoxide, 81 g (0.72 mole) of potassium t-butoxide was added in small portions over 30 minutes and the resultant mixture was stirred at the room temperature for 18 hours. To the obtained reaction mixture, 3 liters of water was added. After the resultant product was dispersed and filtered, crystals were obtained. To the obtained crystals, 3 liters of water was added and the resultant product was dispersed and filtered. The obtained crystals were washed with water and hexane, successively. The crude crystals were then purified by recrystallization from ethyl acetate and 151 g (the yield: 74%) of intermediate B as the object substance was obtained.

Synthesis of Intermediate C

Into a flask, 130 g (0.38 mole) of intermediate B, 143 g (1.54 mole) of aniline, 5.3 g (1.5% by mole) of tris(dibenzylideneacetone)-dipalladium, 2.3 g (3% by mole) of tri-t-butylphosphine, 92.4 g (0.96 mmole) of sodium t-butoxide and 2 liters of dry toluene were added and the resultant mixture was stirred under heating at 100° C. for one night. After the reaction was completed, precipitated crystals were separated by filtration and washed with methanol. The crude crystals were then purified by silica gel column chromatography and 50 g (the yield: 36%) of intermediate C as the object substance was obtained.

Synthesis of Compound (2)

Figure 2:
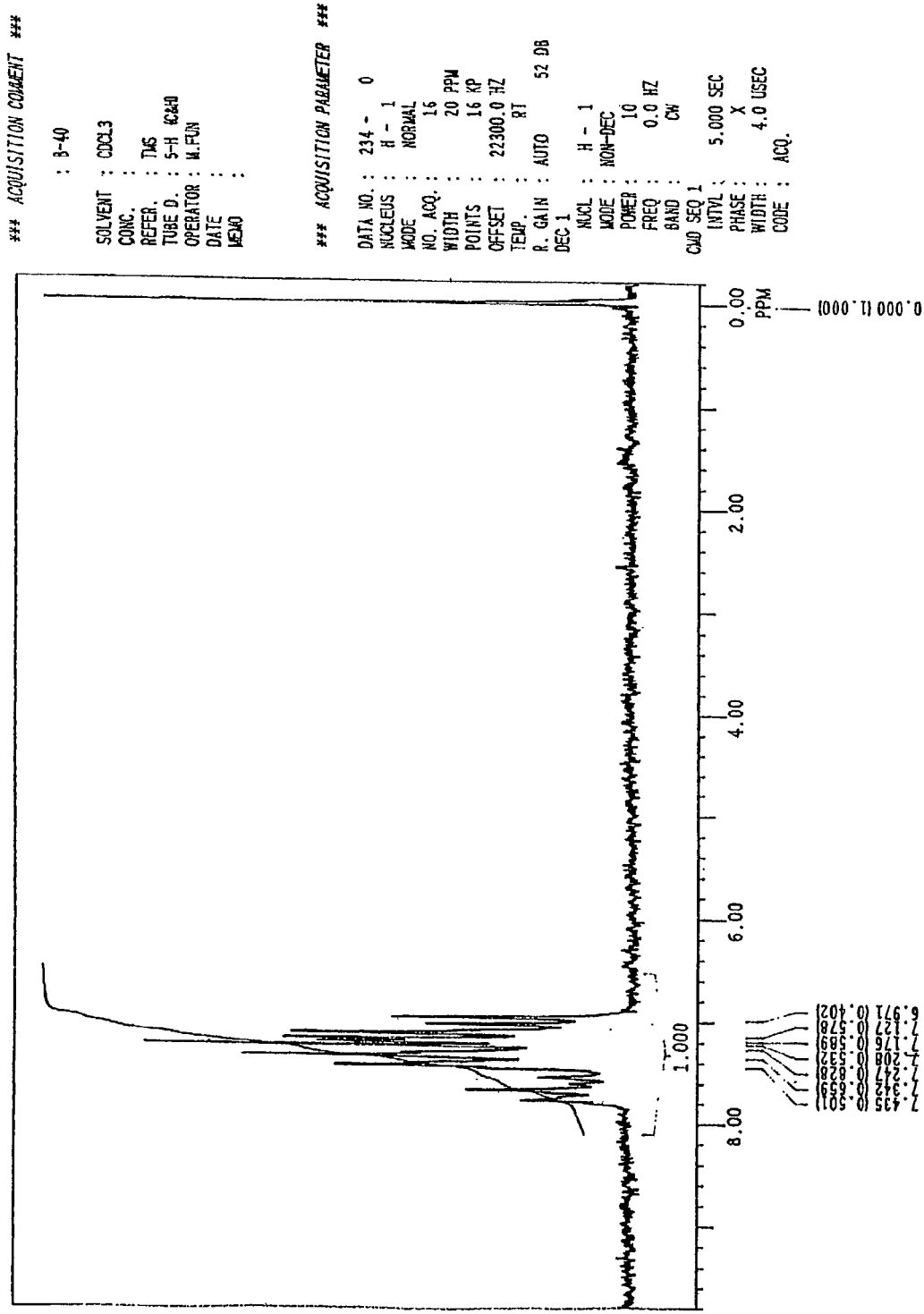
FIG. 2 shows a $^1H_{NMR}$ chart of novel styryl compound (2) of the present invention.

Into a 200 ml three-necked flask equipped with a condenser, 3.6 g (10 mmole) of intermediate C, 4.6 g (22 mmole) of 2-bromonaphthalene, 0.14 g (1.5% by mole) of tris(dibenzylideneacetone)dipalladium, 0.06 g (3% by mole) of tri-t-butylphosphine, 4.2 g (44 mmole) of sodium t-butoxide and 100 ml of dry toluene were placed under argon and the resultant mixture was stirred under heating at 100° C. for one night. After the reaction was completed, precipitated crystals were separated by filtration and washed with 100 ml of methanol and 5.2 g of a yellow powder was obtained. The obtained product was identified to be compound (2) by the measurements in accordance with NMR, IR and FD-MS (the yield: 85%). The NMR chart of compound (2) is shown in FIG. 2.

Synthesis Example 3 (Compound (3))

Compound (3) was synthesized in accordance with the following route of reactions:

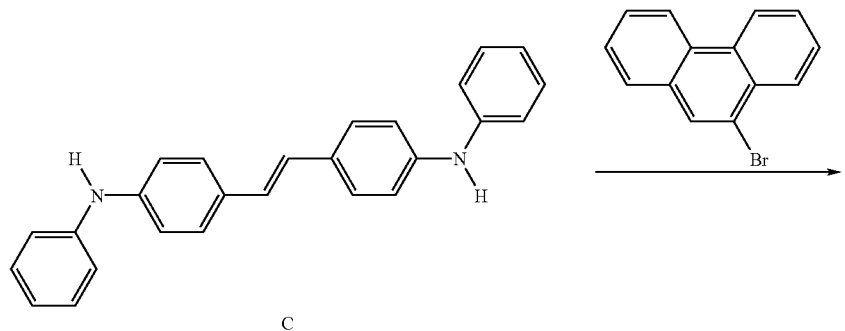

C

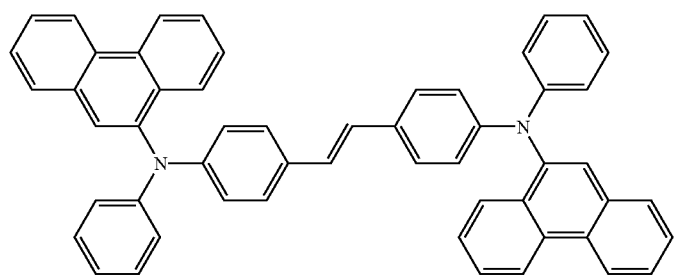

Compound (3)

Figure 3:
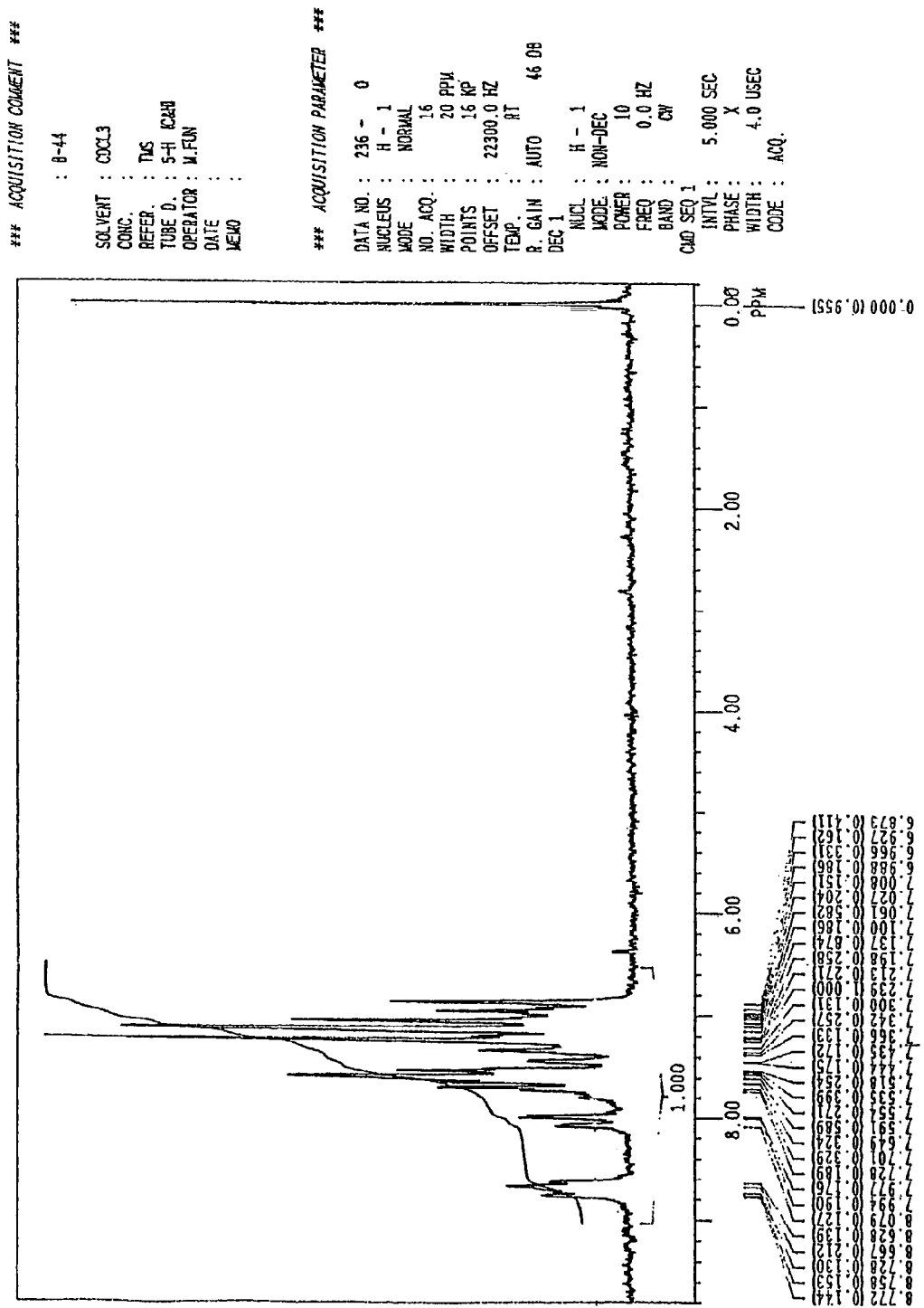
FIG. 3 shows a $^1H_{NMR}$ chart of novel styryl compound (3) of the present invention.

Into a 200 ml three-necked flask equipped with a condenser, 3.6 g (10 mmole) of intermediate C, 5.6 g (22 mmole) of 9-bromophenanthrene, 0.14 g (1.5% by mole) of tris(dibenzylideneacetone)dipalladium, 0.06 g (3% by mole) of tri-t-butylphosphine, 4.2 g (44 mmole) of sodium t-butoxide and 100 ml of dry toluene were placed under argon and the resultant mixture was stirred under heating at 100° C. for one night. After the reaction was completed, precipitated crystals were separated by filtration and washed with 100 ml of methanol and 5.7 g of a yellow powder was obtained. The obtained product was identified to be compound (3) by the measurements in accordance with NMR, IR and FD-MS (the yield: 80%). The NMR chart of compound (3) is shown in FIG. 3.

Synthesis Example 4 (Compound (4))

Compound (4) was synthesized in accordance with the following route of reactions:

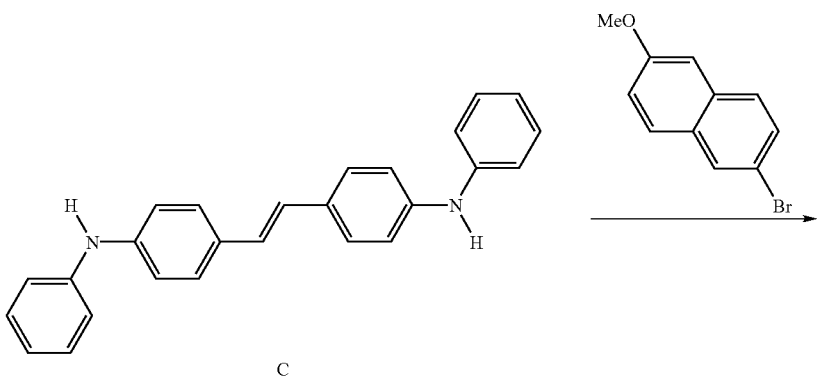

C

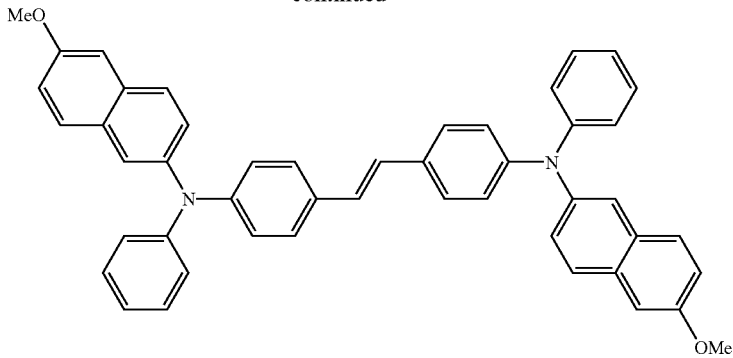

Compound (4)

Figure 4:
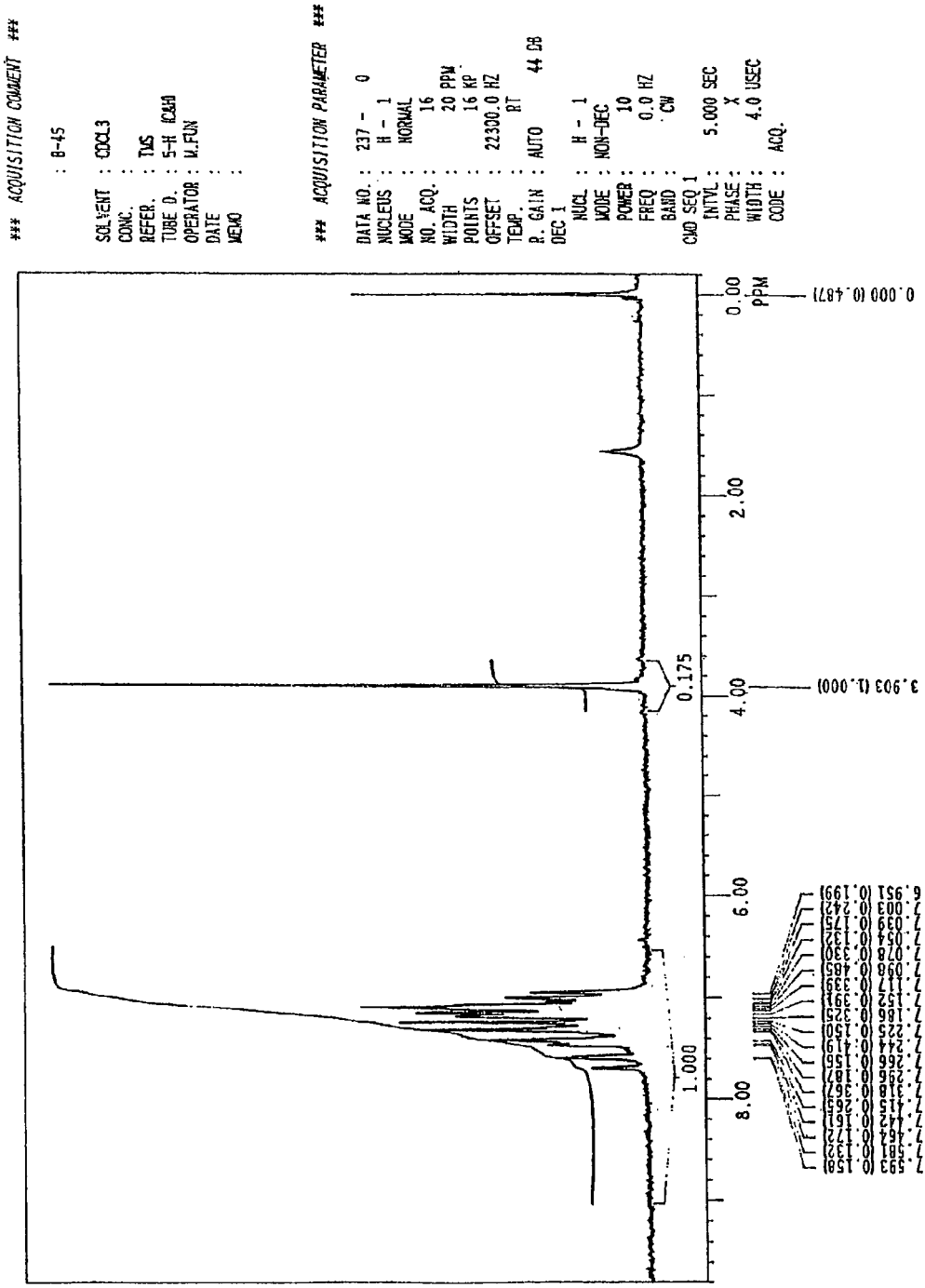
FIG. 4 shows a $^1H_{NMR}$ chart of novel styryl compound (4) of the present invention.

Into a 200 ml three-necked flask equipped with a condenser, 3.6 g (10 mmole) of intermediate C, 5.2 g (22 mmole) of 2-bromo-6-methoxynaphthalene, 0.14 g (1.5% by mole) of tris(dibenzylideneacetone)dipalladium, 0.06 g (3% by mole) of tri-t-butylphosphine, 4.2 g (44 mmole) of sodium t-butoxide and 100 ml of dry toluene were placed under argon and the resultant mixture was stirred under heating at 100° C. for one night. After the reaction was completed, precipitated crystals were separated by filtration and washed with 100 ml of methanol and 5.4 g of a yellow powder was obtained. The obtained product was identified to be compound (4) by the measurements in accordance with NMR, IR and FD-MS (the yield: 80%). The NMR chart of compound (4) is shown in FIG. 4.

Synthesis Example 5 (Compound (5))

Compound (5) was synthesized in accordance with the following route of reactions:

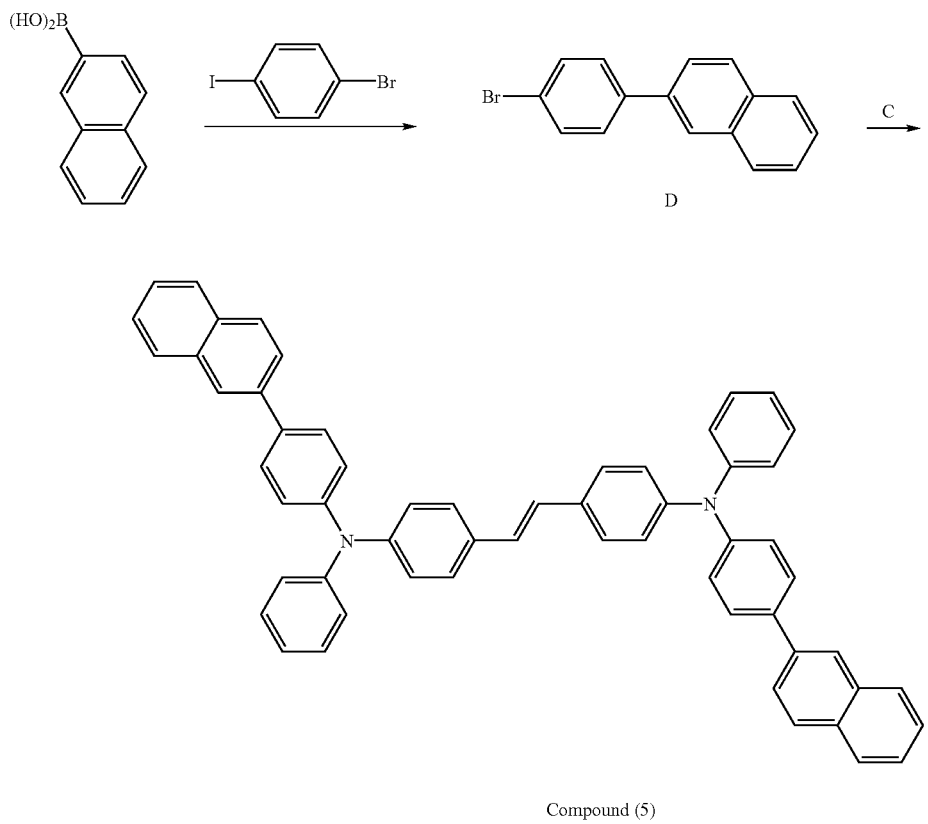

Compound (5)

Synthesis of Intermediate D

Into a 200 ml three-necked flask equipped with a condenser, 12.5 g (44 mmole) of p-bromoiodobenzene, 12.7 g (40 mmole) of 2-naphthylboric acid, 0.7 g (1.5% by mole) of tetrakis(triphenylphosphine)palladium, 0.06 g (0.12 mole) of sodium carbonate, 80 ml of toluene and 60 ml of water were placed and the resultant mixture was stirred under heating for one night. After the reaction was completed, precipitated crystals were separated by filtration and washed with 100 ml of methanol. The crude crystals were purified by recrystallization from ethyl acetate and 9.0 g (the yield: 72%) of intermediate D as the object substance was obtained.

Synthesis of Compound (5)

Figure 5:
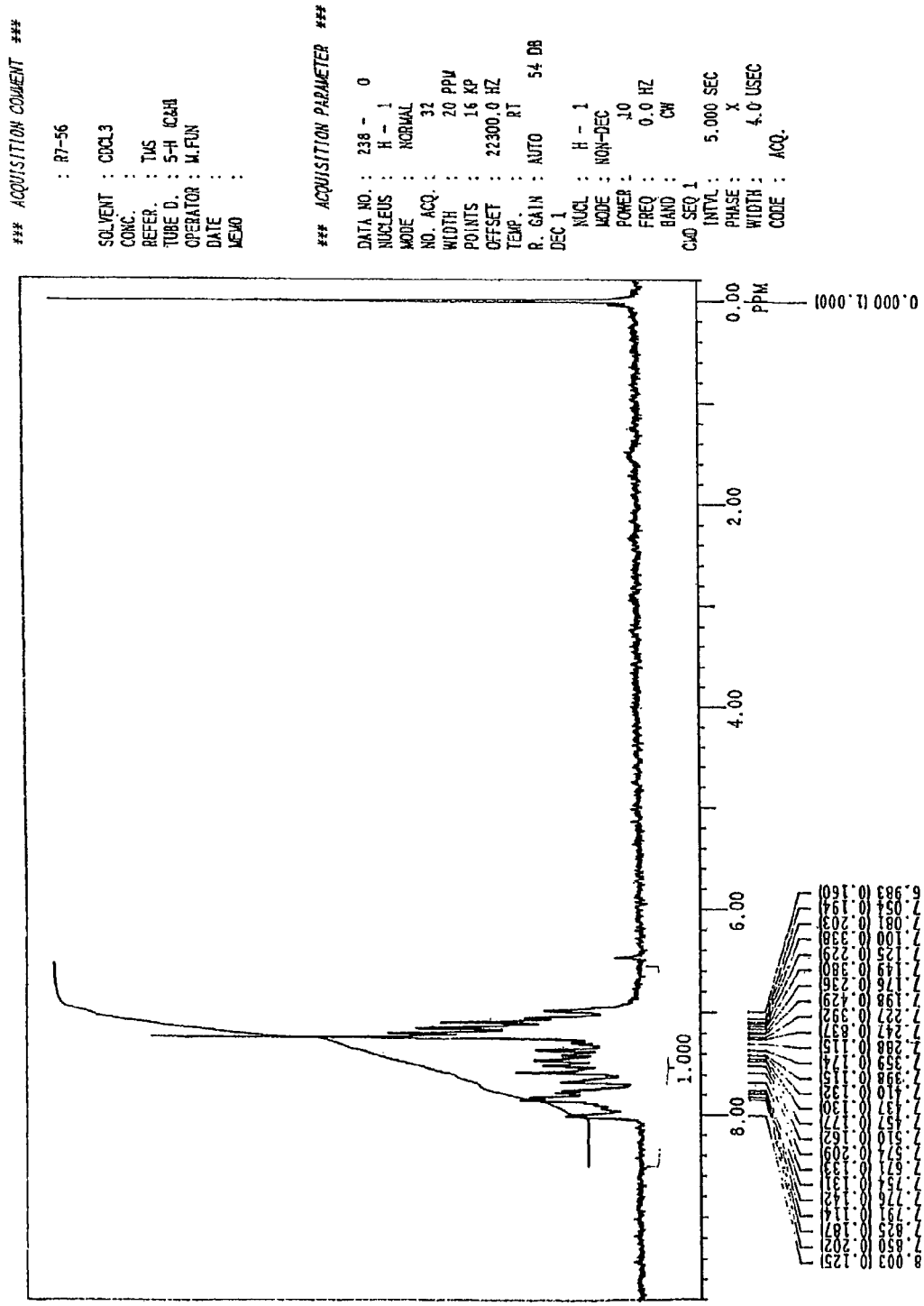
FIG. 5 shows a $^1H_{NMR}$ chart of novel styryl compound (5) of the present invention.

Into a 200 ml three-necked flask equipped with a condenser, 3.6 g (10 mmole) of intermediate C, 6.2 g (22 mmole) of intermediate D, 0.14 g (1.5% by mole) of tris(dibenzylideneacetone)dipalladium, 0.06 g (3% by mole) of tri-t-butylphosphine, 4.2 g (44 mmole) of sodium t-butoxide and 100 ml of dry toluene were placed under argon and the resultant mixture was stirred under heating at 100° C. for one night. After the reaction was completed, precipitated crystals were separated by filtration and washed with 100 ml of methanol and 6.5 g of a yellow powder was obtained. The obtained product was identified to be compound (5) by the measurements in accordance with NMR, IR and FD-MS (the yield: 85%). The NMR chart of compound (5) is shown in FIG. 5.

Example 1

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N'-diphenyl-4-aminophenyl)-N,N'-diephenyl-4,4'-diamino-1,1'-biphenyl (referred to as TPD232, hereinafter) having a thickness of 60 nm was formed so that the formed film covered the transparent electrode. The formed film of TPD232 worked as the first hole injecting layer (the hole transporting layer). Then, on the formed film of TPD232, a film of 4,4'-bis[N-(1-naphthyl)-N-phenylamino]-biphenyl (referred to as NPD, hereinafter) having a thickness of 20 nm was formed. The formed film of NPD worked as the second hole injecting layer (the hole transporting layer). On the formed film of NPD, 4',4''-bis(2,2-diphenylvinyl)-9,10-biphenyl (referred to as DPVBI, hereinafter) and compound (1) synthesized above were binary vacuum vapor deposited so that a film having a thickness of 40 nm and containing 2.5% by weight of compound (1) was formed. The film of DPVBI and compound (1) worked as the light emitting layer. On the film formed above, a film of tris(8-quinolinol)aluminum (referred to as Alq, hereinafter) having a thickness of 20 nm was formed. The film of Alq worked as the electron injecting layer. Thereafter, Li (the source of lithium: manufactured by SAES GETTERS Company) and Alq were binary vapor deposited and an Alq:Li film was formed as the electron injecting layer (the cathode). On the formed Alq:Li film, metallic aluminum was vapor deposited to form a metal cathode and an organic El device was prepared.

When a direct current voltage of 6 V was applied to the organic EL device prepared above, blue light of a high purity having a chromaticity of (0.15, 0.16) was emitted at a luminance of 275 cd/m$^2$ and an efficiency of light emission of 4.5 cd/A. The half-life was as long as 12,000 hours in the life test in which the device was driven under a constant current at an initial luminance of 100 cd/m$^2$.

Example 2

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of TPD232 having a thickness of 60 nm was formed so that the formed film covered the transparent electrode. The formed film of TPD232 worked as the first hole injecting layer (the hole transporting layer). Then, on the formed film of TPD232, a film of NPD having a thickness of 20 nm was formed. The formed film of NPD worked as the second hole injecting layer (the hole transporting layer). On the formed film of NPD, 4',4''-bis(2,2-diphenylvinyl)-9,10-biphenylanthracene (referred to as DPVDPAN, hereinafter) and compound (2) synthesized above were binary vacuum vapor deposited so that a film having a thickness of 40 nm and containing 2.5% by weight of compound (2) was formed. The film of DPVDPAN and compound (2) worked as the light emitting layer. On the film formed above, a film of Alq having a thickness 20 nm was formed. The film of Alq worked as the electron injecting layer. Thereafter, Li (the source of lithium: manufactured by SAES GETTERS Company) and Alq were binary vapor deposited and an Alq:Li film was formed as the electron injecting layer (the cathode). On the Alq:Li film, metallic aluminum was vapor deposited to form a metal cathode and an organic El device was prepared.

When a direct current voltage of 6 V was applied to the organic EL device prepared above, blue light of a high purity having a chromaticity of (0.15, 0.16) was emitted at a luminance of 343 cd/m$^2$ and an efficiency of light emission of 4.1 cd/A. This device exhibited a spectrum having a peak at about 450 nm and was useful as the light emitting device emitting blue light. The half-life was as long as 9,800 hours in the life test in which the device was driven under a constant current at an initial luminance of 100 cd/m$^2$.

Example 3

An organic EL device was prepared in accordance with the same procedures as those conducted in Example 2 except that compound (2) was replaced with compound (3).

When a direct current voltage of 6 V was applied to the organic EL device prepared above, blue light of a high purity having a chromaticity of (0.15, 0.18) was emitted at a luminance of 103 cd/m$^2$ and an efficiency of light emission of 4.4 cd/A. This device exhibited a spectrum having a peak at about 460 nm and was useful as the light emitting device emitting blue light. The half-life was as long as 16,000 hours in the life test in which the device was driven under a constant current at an initial luminance of 100 cd/m$^2$.

Example 4

An organic EL device was prepared in accordance with the same procedures as those conducted in Example 2 except that compound (2) was replaced with compound (4).

When a direct current voltage of 6 V was applied to the organic EL device prepared above, blue light of a high purity having a chromaticity of (0.15, 0.19) was emitted at a luminance of 62 cd/m² and an efficiency of light emission of 4.5 cd/A. This device exhibited a spectrum having a peak at about 460 nm and was useful as the light emitting device emitting blue light. The half-life was as long as 18,000 hours in the life test in which the device was driven under a constant current at an initial luminance of 100 cd/m².

Comparative Example 1

An organic EL device was prepared in accordance with the same procedures as those conducted in Example 1 except that compound (1) was replaced with the following compound:

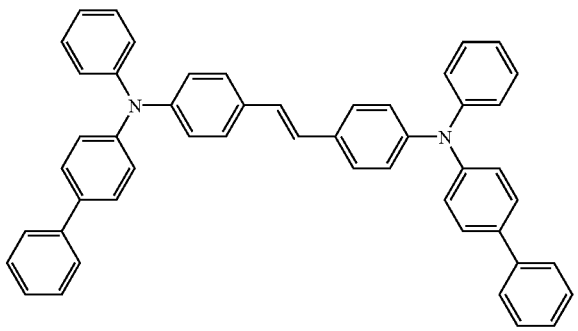

When a direct current voltage of 6 V was applied to the organic EL device prepared above, blue light was emitted at an efficiency of light emission as low as 3 cd/A. The half-life was as short as 2,000 hours in the life test in which the device was driven under a constant current at an initial luminance of 100 cd/m².

Comparative Example 2

An organic EL device was prepared in accordance with the same procedures as those conducted in Example 1 except that compound (1) was replaced with the following compound:

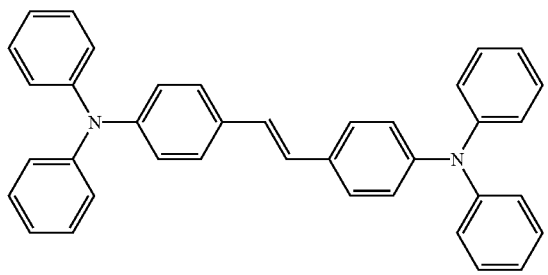

When a direct current voltage of 6 V was applied to the organic EL device prepared above, blue light was emitted at an efficiency of light emission as low as 2.7 cd/A. The half-life was as short as 2,300 hours in the life test in which the device was driven under a constant current at an initial luminance of 100 cd/m².

INDUSTRIAL APPLICABILITY

As described in detail in the above, the organic electroluminescence device utilizing the novel styryl compound of the present invention has excellent heat resistance, a high efficiently of light emission and a long life and emits blue light of a high purity.

Therefore, the organic electroluminescence device of the present invention is useful for a planar light emitting member for wall televisions and a light source for a back light of displays.

What is claimed is:

1. An electroluminescence device comprising a pair of electrodes and a film of organic compounds that is disposed between the pair of electrodes and comprises a single layer or a plurality of layers comprising at least a light emitting layer, wherein at least one of the layers of the film of organic compounds comprises a novel styryl compound represented by the following general formula (1):

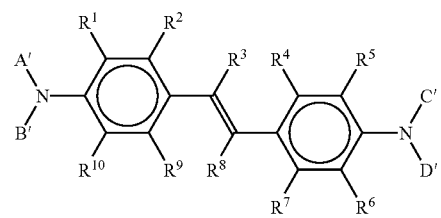

(2)

wherein $R^1$ to $R^{10}$ each independently represent hydrogen atom, a substituted or unsubstituted alkyl group having 1 to 30 carbon atoms, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^3$ to $R^{10}$ may be bonded to each other and form a saturated or unsaturated carbon ring and the groups represented by $R^1$ and $R^2$ are not bonded together to each other;

A, B, C and D each independently represent a substituted or unsubstituted alkyl group having 1 to 20 carbon atoms or a substituted or unsubstituted aryl group having 6 to 40 carbon atoms, and at least two of A, B, C and D each represent a group represented by —$Ar^1$—$Ar^2$, $Ar^1$ representing a substituted or unsubstituted phenyl group or naphthalene group and $Ar^2$ representing a substituted or unsubstituted aryl group having 6 to 34 carbon atoms, excluding (1) a case in which A and C represent biphenyl group and B and D represent phenyl group and (2) a case in which any of A, B, C, and D represents a substituted or unsubstituted pyrene.

2. An electroluminescence device comprising a pair of electrodes and a film of organic compounds that is disposed between the pair of electrodes and comprises a single layer or a plurality of layers comprising at least a light emitting layer, wherein at least one of the layers of the film of organic compounds comprises a novel styryl compound represented by the following general formula (2):

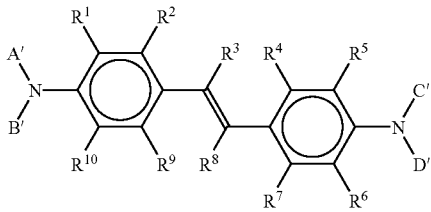

(2)

wherein $R^1$ to $R^{10}$ each independently represent hydrogen atom, a substituted or unsubstituted alkyl group having 1 to 30 carbon atoms, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^3$ to $R^{10}$ may be bonded to each other and form a saturated or unsaturated carbon ring and the groups represented by $R^1$ and $R^2$ are not bonded together to each other; and A', B', C' and D' each independently represent a substituted or unsubstituted alkyl group having 1 to 20 carbon atoms or a substituted or unsubstituted aryl group having 6 to 40 carbon atoms, and A' and C' additionally each represent a substituted or unsubstituted condensed hydrocarbon group having 2 to 5 rings, excluding a case in which any of A', B', C', and D' represents a substituted or unsubstituted pyrene.

3. An electroluminescence device comprising a pair of electrodes and a film of organic compounds that is disposed between the pair of electrodes and comprises a single layer or a plurality of layers comprising at least a light emitting layer, wherein the light emitting layer comprises a novel styryl compound represented by the following general formula (1):

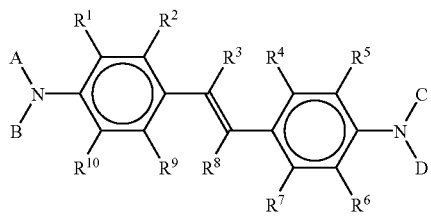

(1)

wherein $R^1$ to $R^{10}$ each independently represent hydrogen atom, a substituted or unsubstituted alkyl group having 1 to 30 carbon atoms, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^3$ to $R^{10}$ may be bonded to each other and form a saturated or unsaturated carbon ring and the groups represented by $R^1$ and $R^2$ are not bonded together to each other;

A, B, C and D each independently represent a substituted or unsubstituted alkyl group having 1 to 20 carbon atoms or a substituted or unsubstituted aryl group having 6 to 40 carbon atoms, and at least two of A, B, C and D each represent a group represented by —$Ar^1$—$Ar^2$, $Ar^1$ representing a substituted or unsubstituted phenyl group or naphthalene group and $Ar^2$ representing a substituted or unsubstituted aryl group having 6 to 34 carbon atoms, excluding (1) a case in which A and C represent biphenyl group and B and D represent phenyl group, and (2) a case in which any of A, B, C, and D represents a substituted or unsubstituted pyrene.

4. An electroluminescence device according to claim 3, wherein a layer of an inorganic compound is disposed between the light emitting layer and the electrode.

5. An electroluminescence device comprising a pair of electrodes and a film of organic compounds that is disposed between the pair of electrodes and comprises a single layer or a plurality of layers comprising at least a light emitting layer, wherein the light emitting layer comprises a novel styryl compound represented by the following general formula (2):

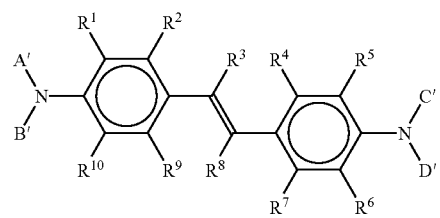

(2)

wherein $R^1$ to $R^{10}$ each independently represent hydrogen atom, a substituted or unsubstituted alkyl group having 1 to 30 carbon, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^3$ to $R^{10}$ may be bonded to each other and form a saturated or unsaturated carbon ring and the groups represented by $R^1$ and $R^2$ are not bonded together to each other; and A', B', C' and D' each independently represent a substituted or unsubstituted alkyl group having 1 to 20 carbon atoms or a substituted or unsubstituted aryl group having 6 to 40 carbon atoms, and A' and C' additionally each represent a substituted or unsubstituted condensed hydrocarbon group having 2 to 5 rings, excluding a case in which any of A', B', C', and D' represents a substituted or unsubstituted pyrene.

6. An electroluminescence device according to claim 5, wherein a layer of an inorganic compound is disposed between the light emitting layer and the electrode.

7. An electroluminescence device comprising a pair of electrodes and a film of organic compounds that is disposed between the pair of electrodes and comprises a single layer or a plurality of layers comprising at least a light emitting layer, wherein an electron injecting layer or a hole injecting layer comprises a novel styryl compound represented by the following general formula (1):

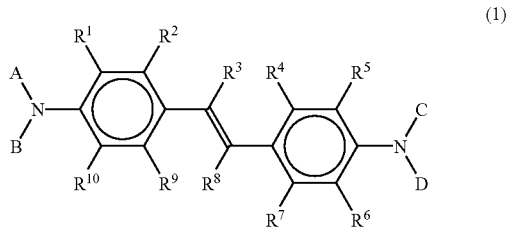

(1)

wherein $R^1$ to $R^{10}$ each independently represent hydrogen atom, a substituted or unsubstituted alkyl group having 1 to 30 carbon atoms, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^3$ to $R^{10}$ may be bonded to each other and form a saturated or unsaturated carbon ring and the groups represented by $R^1$ and $R^2$ are not bonded together to each other;

A, B, C and D each independently represent a substituted or unsubstituted alkyl group having 1 to 20 carbon atoms or a substituted or unsubstituted aryl group having 6 to 40 carbon atoms, and at least two of A, B, C and D each represent a group represented by —$Ar^1$—$Ar^2$, $Ar^1$ representing a substituted or unsubstituted phenyl group or naphthalene group and $Ar^2$ representing a substituted or unsubstituted aryl group having 6 to 34 carbon atoms, excluding (1) a case in which A and C represent biphenyl group and B and D represent phenyl group, and (2) a case in which any of A, B, C, and D represents a substituted or unsubstituted pyrene.

8. An electroluminescence device comprising a pair of electrodes and a film of organic compounds that is disposed between the pair of electrodes and comprises a single layer or a plurality of layers comprising at least a light emitting layer, wherein an electron injecting layer or a hole injecting layer comprises a novel styryl compound represented by the following general formula (2):

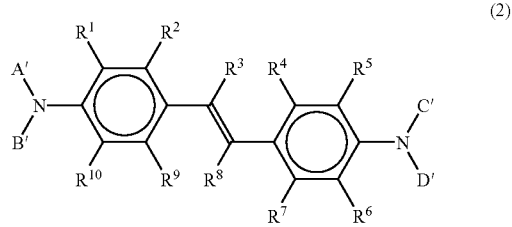

(2)

wherein $R^1$ to $R^{10}$ each independently represent hydrogen atom, a substituted or unsubstituted alkyl group having 1 to 30 carbon atoms, a substituted or unsubstituted alkoxyl group having 1 to 30 carbon atoms, a substituted or unsubstituted aryl group having 6 to 20 carbon atoms, a substituted or unsubstituted aryloxyl group having 6 to 18 carbon atoms, a substituted or unsubstituted condensed polycyclic group having 6 to 30 carbon atoms, a substituted or unsubstituted heterocyclic group having 5 to 30 carbon atoms, amino group, an alkylamino group having 2 to 30 carbon atoms, an arylamino group having 6 to 30 carbon atoms, cyano group, nitro group, hydroxyl group or a halogen atom, and adjacent groups among groups represented by $R^3$ to $R^{10}$ may be bonded to each other and form a saturated or unsaturated carbon ring and the groups represented by $R^1$ and $R^2$ are not bonded together to each other; and A', B', C' and D' each independently represent a substituted or unsubstituted alkyl group having 1 to 20 carbon atoms or a substituted or unsubstituted aryl group having 6 to 40 carbon atoms, and A' and C' additionally each represent a substituted or unsubstituted condensed hydrocarbon group having 2 to 5 rings, excluding a case in which any of A', B', C', and D' represents a substituted or unsubstituted pyrene.

* * * * *